(12) United States Patent
Godfrey (10) Patent No.: US 11,278,459 B2
(45) Date of Patent: Mar. 22, 2022

(54) METHODS AND APPARATUS FOR A DUAL-USE DISPOSABLE SANITARY GARMENT

(71) Applicant: Mary Ann Godfrey, Tempe, AZ (US)

(72) Inventor: Mary Ann Godfrey, Tempe, AZ (US)

( * ) Notice: Subject to any disclaimer, the term of this patent is extended or adjusted under 35 U.S.C. 154(b) by 630 days.

(21) Appl. No.: 16/353,151

(22) Filed: Mar. 14, 2019

(65) Prior Publication Data

US 2020/0289345 A1 Sep. 17, 2020

(51) Int. Cl.
*A61F 13/47* (2006.01)
*A61F 13/551* (2006.01)
*A61F 13/56* (2006.01)

(52) U.S. Cl.
CPC ...... *A61F 13/5611* (2013.01); *A61F 13/4704* (2013.01); *A61F 13/5514* (2013.01); *A61F 13/5616* (2013.01); *A61F 2013/4708* (2013.01)

(58) Field of Classification Search
CPC .. A61F 13/4704; A61F 13/493; A61F 13/505; A61F 13/55115; A61F 13/5514; A61F 13/55145; A61F 13/5519; A61F 13/5611; A61F 13/5616; A61F 2013/4708; A61F 2013/49063; A61F 2013/5055
See application file for complete search history.

(56) References Cited

U.S. PATENT DOCUMENTS

| | | |
|---|---|---|
| 2,450,789 A | 10/1948 | Frieman |
| 4,560,381 A | 12/1985 | Southwell |
| 4,804,380 A | 2/1989 | Lassen et al. |
| 4,940,463 A | 7/1990 | Leathers et al. |
| 5,241,710 A | 9/1993 | Lockhart |
| 5,711,034 A | 1/1998 | Cillik |
| 5,733,274 A | 3/1998 | Osborn, III |
| 5,944,708 A | 8/1999 | Philpott |
| 6,240,569 B1 | 6/2001 | Van Gompel et al. |
| 6,251,097 B1 | 6/2001 | Kline et al. |
| 6,309,378 B1 * | 10/2001 | Costa .................. A61F 13/5616 604/385.04 |
| 6,783,487 B2 | 8/2004 | Duhm et al. |
| D585,182 S | 1/2009 | Hodges et al. |
| 8,343,127 B1 | 1/2013 | Dimitrijevs et al. |
| 9,132,049 B2 | 9/2015 | Popp et al. |
| 9,913,766 B2 * | 3/2018 | Petersen ................. A61F 13/74 |

(Continued)

FOREIGN PATENT DOCUMENTS

| | | |
|---|---|---|
| CN | 204246335 | 4/2015 |
| EP | 1016392 A1 | 12/1998 |

(Continued)

*Primary Examiner* — Catharine L Anderson
*Assistant Examiner* — Lynne Anderson
(74) *Attorney, Agent, or Firm* — Noblitt & Newson, PLLC (57) ABSTRACT

An apparatus for a dual-use disposable sanitary garment according to various aspects of the present technology include an absorbent layer coupled to a wearable garment. The wearable garment is folded inward and sealed within a pouch portion adjacent to the absorbent layer. The wearable garment is enclosed within the pouch portion by a removable adhesive layer that is configured to either be kept in place allowing the entire garment to be used as a commonly known sanitary napkin or the adhesive can be removed thereby allowing the wearable garment to be unfolded and worn. The entire sanitary garment may then be disposed after use.

20 Claims, 8 Drawing Sheets

(56) References Cited

U.S. PATENT DOCUMENTS

| | | |
|---|---|---|
| 2004/0025219 A1 | 2/2004 | McQueen |
| 2005/0090795 A1 | 4/2005 | Coleman |
| 2005/0137548 A1 | 6/2005 | Riley |
| 2005/0203480 A1 | 9/2005 | Chang |
| 2007/0118092 A1 | 5/2007 | Blanco |
| 2009/0082749 A1 | 3/2009 | Scott et al. |
| 2009/0182296 A1 | 7/2009 | Dennis et al. |
| 2009/0240226 A1 | 9/2009 | Fields et al. |
| 2010/0318051 A1 | 12/2010 | McCourt et al. |

FOREIGN PATENT DOCUMENTS

| | | |
|---|---|---|
| FR | 2716368 A1 | 8/1995 |
| JP | 3103429 | 8/2004 |
| JP | 6342675 B2 | 9/2015 |

\* cited by examiner

FIG. 15

METHODS AND APPARATUS FOR A DUAL-USE DISPOSABLE SANITARY GARMENT

BACKGROUND OF THE TECHNOLOGY

Disposable sanitary napkins and pads are one of the most commonly used feminine hygiene articles during a woman's menstrual cycle. Other options include tampons and non-disposable napkins and pads. A common element of all options is the use of an absorbent layer directed towards absorbing menstrual fluid and preventing other articles of clothing from being stained.

The various types of feminine hygiene articles generally function as intended, but with varying level of success. For example, a sanitary napkin may not provide adequate absorption and result in the staining of an undergarment being worn at the same time as the sanitary napkin. This may result in the undergarment requiring additional laundering to remove any staining. One solution to this problem is the use of disposable undergarments that include an integrated sanitary pad. This combined disposable product provides the benefit of a disposable product but may suffer from other issues such as comfort, manufacturability, or performance.

SUMMARY OF THE TECHNOLOGY

An apparatus for a dual-use disposable sanitary garment according to various aspects of the present technology include an absorbent layer coupled to a wearable garment. The wearable garment is folded inward and sealed within a pouch portion adjacent to the absorbent layer. The wearable garment is enclosed within the pouch portion by a removable adhesive layer that is configured to either be kept in place allowing the entire garment to be used as a commonly known sanitary napkin or the adhesive can be removed thereby allowing the wearable garment to be unfolded and worn. The entire sanitary garment may then be disposed after use.

BRIEF DESCRIPTION OF THE DRAWINGS

A more complete understanding of the present technology may be derived by referring to the detailed description and claims when considered in connection with the following illustrative figures. In the following figures, like reference numbers refer to similar elements and steps throughout the figures.

Elements and steps in the figures are illustrated for simplicity and clarity and have not necessarily been rendered according to any particular sequence. For example, steps that may be performed concurrently or in a different order are illustrated in the figures to help to improve understanding of embodiments of the present technology.

DETAILED DESCRIPTION OF EXEMPLARY EMBODIMENTS

The present technology may be described in terms of functional block components and various processing steps. Such functional blocks may be realized by any number of components configured to perform the specified functions and achieve the various results. For example, the present technology may employ various materials, fabrics, absorbents, and geometries, which may carry out a variety of operations. In addition, the technology described is merely one exemplary application for the disclosed device. Further, the present technology may employ any number of conventional techniques for absorbing bodily fluids or methods of connection.

Methods and apparatus for a dual-use disposable sanitary garment according to various aspects of the present technology may operate in conjunction with any textile, fabric, or material such as: cotton, silk, rayon, or polyester used to form an article of clothing such as a pair of shorts or underpants. Various representative implementations of the present technology may be applied to any type of undergarment, sanitary napkin, or article of clothing to provide a disposable garment useful for absorbing bodily fluids.

Referring to FIGS. 1-4, a convertible sanitary garment 100 may comprise a body having an absorbent layer 102 and an opposing selectively usable garment portion 104. The garment portion 104 may be covered by one or more removable layers 106, 108 that are configured to allow the garment portion 104 to be used in a preferred manner.

The absorbent layer 102 may comprise one or more materials commonly used in traditional sanitary napkins or pads such as: cellulose fiber; cotton; polymers; and/or plastics that allow the absorbent layer 102 to absorb bodily fluids such as menstrual discharge, blood, or the like. For example, referring now to FIGS. 12 and 13, the absorbent layer 102 may comprise a liquid pervious top surface or sheet 1202, a liquid impervious bottom surface or sheet 1204, and an absorbent core material 1206 disposed between the liquid pervious top sheet 1202 and the liquid impervious bottom sheet 1204. The absorbent layer 102 may be flexible to allow the convertible sanitary garment 100 to fit against or generally conform to varying anatomies. In addition, the absorbent layer 102 may be stretchable along its length or width to allow the convertible sanitary garment 100 to further adjust to a user's anatomy.

Figure 12:
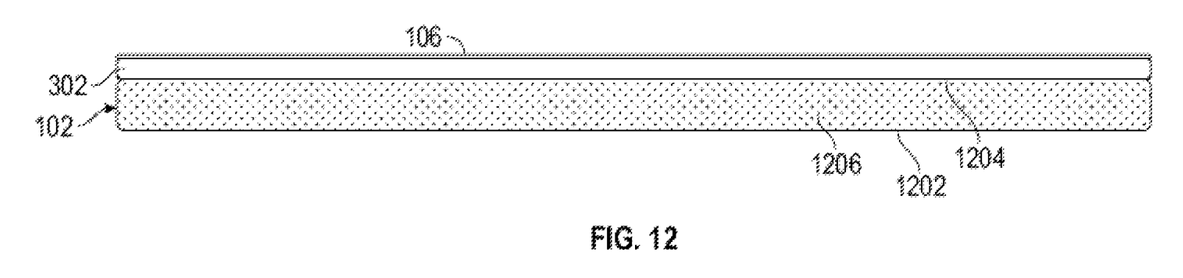
FIG. 12 representatively illustrates a side view of the convertible sanitary garment in accordance with an exemplary embodiment of the present technology.
Figure 13:
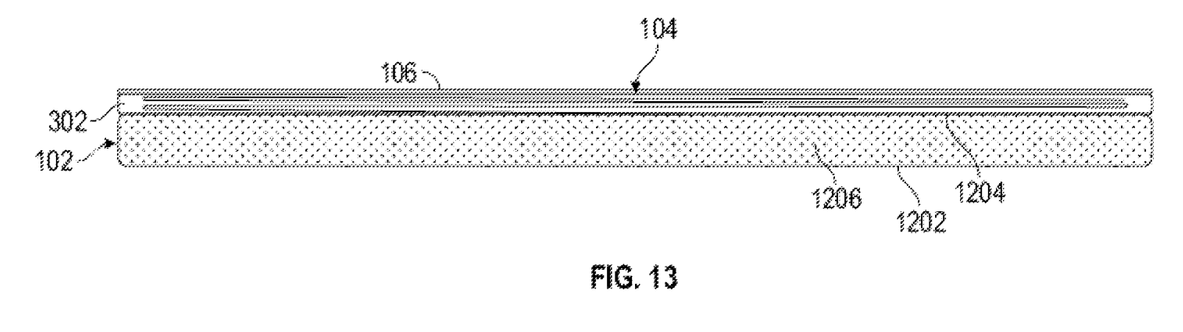
FIG. 13 representatively illustrates a cross-section view across line A-A of FIG. 2 in accordance with an exemplary embodiment of the present technology.

The liquid pervious top sheet 1202 may comprise any suitable material configured to allow a fluid to pass into the absorbent core material 1206. In one embodiment, the liquid pervious top sheet 1202 may comprise a first outermost surface of the absorbent core material 1206. In a second embodiment, the liquid pervious top sheet 1202 may comprise a sheet disposed along an outermost surface of the absorbent core material 1206 that is configured to allow fluid to flow unidirectionally into the absorbent core material 1206 but prevent the fluid from flowing back out of the liquid pervious top sheet 1202.

The liquid impervious bottom sheet 1204 may comprise any suitable material for preventing the flow of fluid out of a second outermost surface of the absorbent core material 1206 that is opposite the first outermost surface of the absorbent core material 1206 adjacent the liquid pervious top sheet 1202. For example, in one embodiment, the liquid impervious bottom sheet 1204 may comprise a plastic sheet or layer to act as a fluid barrier disposed along the second outermost surface of the absorbent core material 1206.

The absorbent core material 1206 may comprise any suitable material or combination of materials suitably adapted to absorb and trap a fluid within the absorbent layer 102. Materials such as cellulose, cotton, super absorbent polymers, and/or hydrogels may be used, at least in part, to form the absorbent core material 1206.

Referring now to FIGS. 1-8, the garment portion 104 may comprise a wearable garment such as a pair of panties, undergarments, or shorts coupled to a surface of the liquid impervious bottom sheet 1204 opposite the absorbent core material 1206. The garment portion 104 is positioned such that the liquid pervious top sheet 1202 is positioned against a user's anatomy during use.

The garment portion 104 may comprise any material or fabric suitable for an article of clothing. The garment portion 104 may comprise a thin layer or material or fabric relative to a thickness of the absorbent layer 102 or a thickness of traditional undergarments. Thinner layers of fabrics may help maintain a low profile of the convertible sanitary garment 100 prior to use or when being used in a desired manner.

The material or fabric may also be stretchable to allow the wearable garment to fit multiple sizes or otherwise be custom fit to a user. In one embodiment, the garment portion 104 may be configured to allow the wearable garment to be assembled in such a manner that the user is able to custom fit the wearable garment to their anatomy. Alternatively, in a second embodiment, the garment portion 104 may comprise a material or fabric that is stretchable enough to comfortably allow the wearable garment to stretch between two to four sizes. For example, the fabric may comprise a thin layer of a soft stretchable fiber such as rayon, cotton, lycra, spandex blend, or the like that will allow the garment portion 104 to stretch between two different sizes, such as: extra-small and small, small and medium, large and extra-large, etc.

One or more sections of the garment portion 104 are configured to be folded inward toward a crotch section having an area defined by a size and shape of the liquid impervious bottom sheet 1204. The crotch section is coupled to the liquid impervious bottom sheet 1204 to secure the garment portion 104 to the absorbent layer 102. The crotch section may be coupled to the liquid impervious bottom sheet 1204 by any suitable method. In one embodiment the crotch section may be coupled to the liquid impervious bottom sheet 1204 by an adhesive. In a second embodiment the crotch section may be sewn or otherwise stitched to the liquid impervious bottom sheet 1204. In a third embodiment, the crotch section may be removably coupled to the liquid impervious bottom sheet 1204 such that the entire garment portion 104 may be selectively removed from the absorbent layer 102 and used independently. For example, the crotch section may be coupled to the liquid impervious bottom sheet 1204 with a non-permanent adhesive that may allow the garment portion 104 to be peeled away from the absorbent layer 102.

The entire garment portion 104 may be held, constrained, or otherwise folded within the area of the crotch section by a removable adhesive layer 108. The removable adhesive layer 108 may comprise any suitable device or system for covering the garment portion 104 such as a removable sheet, panel, or cover. The removable adhesive layer 108 may also comprise any suitable material that allows the convertible sanitary garment 100 to retain its flexibility during storage and/or use. For example, in one embodiment, the removable adhesive layer 108 may comprise a thin clear or opaque plastic sheet. Alternatively, the removable adhesive layer 108 may comprise a soft fabric material.

Referring now to FIGS. 3-5, 9 and 10, the removable adhesive layer 108 is configured to enclose and seal the garment portion 104 until a user chooses to wear the garment portion 104. In one embodiment, the removable adhesive layer 108 may comprise a first surface facing the garment portion 104, wherein a portion of the first surface is removably coupled to an outer periphery of the liquid impervious bottom sheet 1204 to form a pouch or compartment area for containing the garment portion 104. For example, the removable adhesive layer 108 be adhered to the outer periphery of the liquid impervious bottom sheet 1204 and be configured to be selectively removed or detached from the of the liquid impervious bottom sheet 1204 by the user to allow the garment portion 104 to be unfolded and worn.

Figure 1:
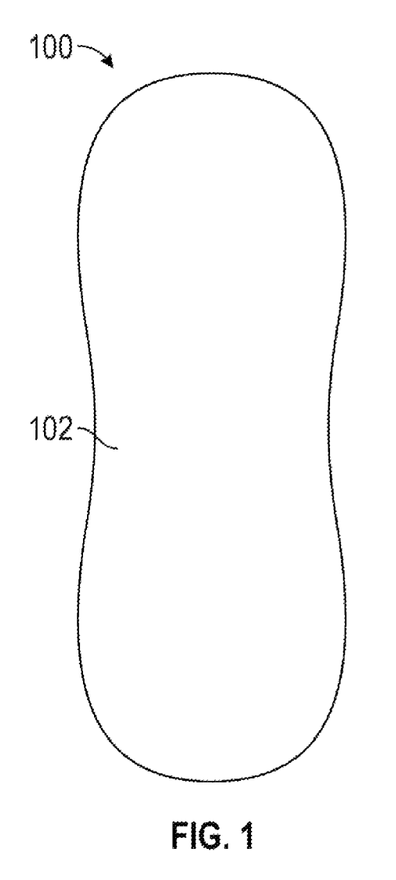
FIG. 1 representatively illustrates a bottom view of a convertible sanitary garment in accordance with an exemplary embodiment of the present technology.
Figure 2:
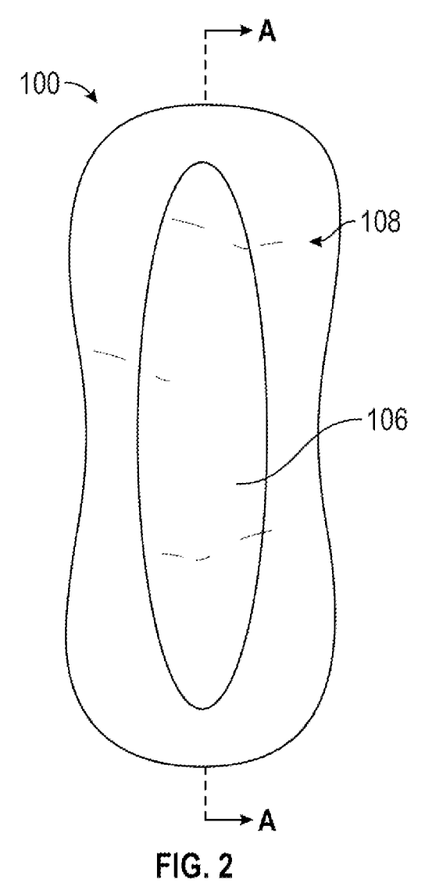
FIG. 2 representatively illustrates a top view of the convertible sanitary garment in accordance with an exemplary embodiment of the present technology.
Figure 3:
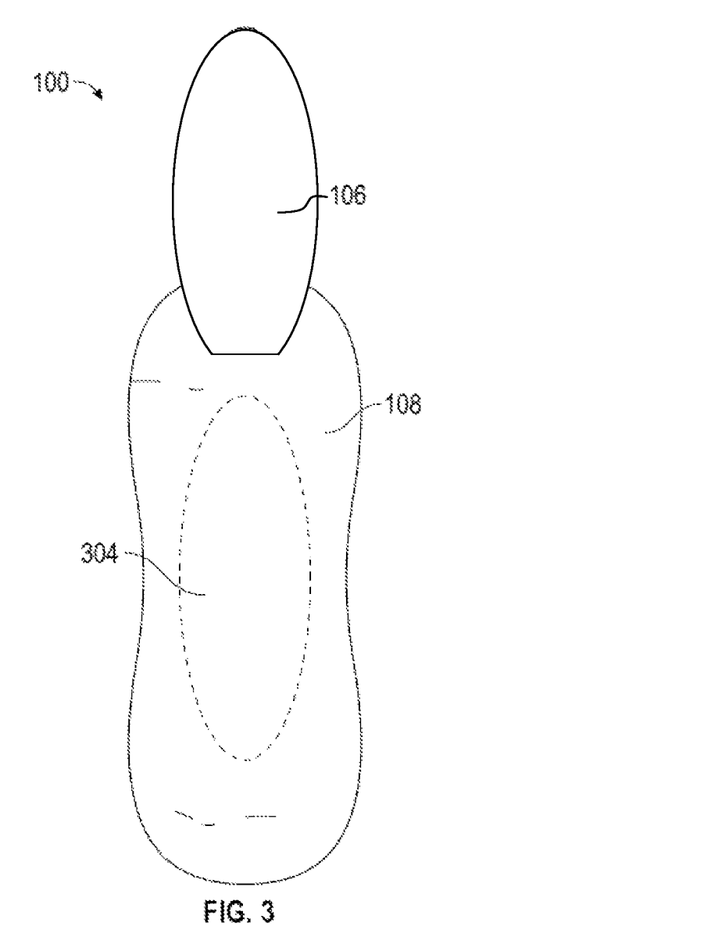
FIG. 3 representatively illustrates a top view of the convertible sanitary garment with an adhesive cover removed in accordance with an exemplary embodiment of the present technology.
Figure 4:
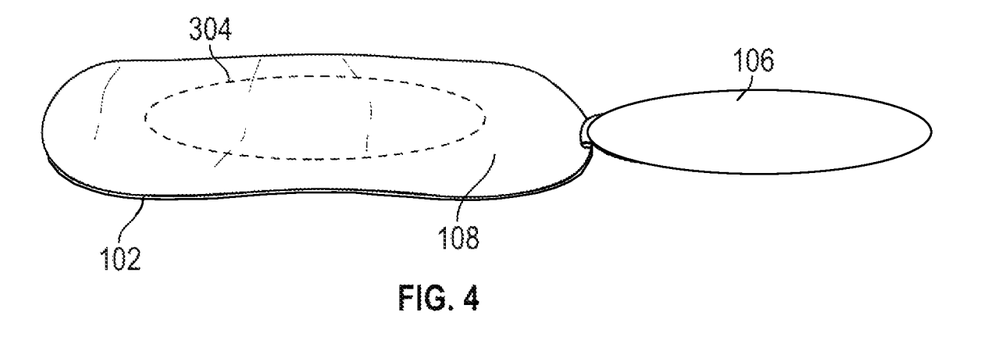
FIG. 4 representatively illustrates a side perspective view of the convertible sanitary garment with an adhesive cover removed in accordance with an exemplary embodiment of the present technology.
Figure 5:
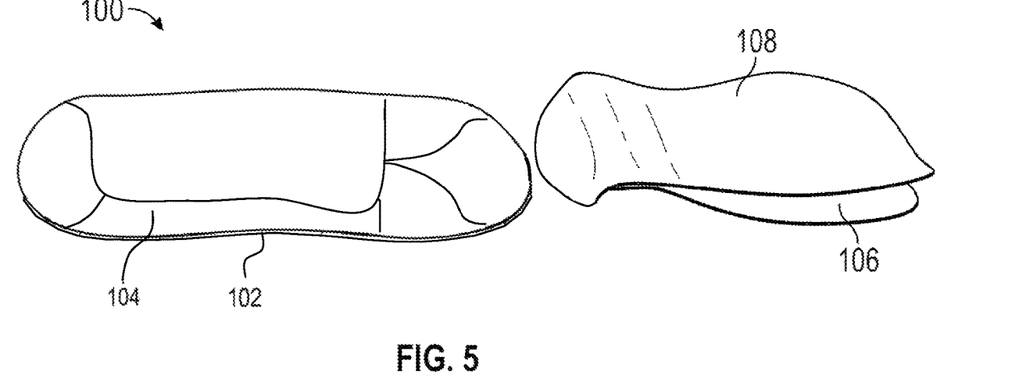
FIG. 5 representatively illustrates a side perspective rear view of the convertible sanitary garment with the adhesive cover and an adhesive layer removed in accordance with an exemplary embodiment of the present technology.
Figure 6:
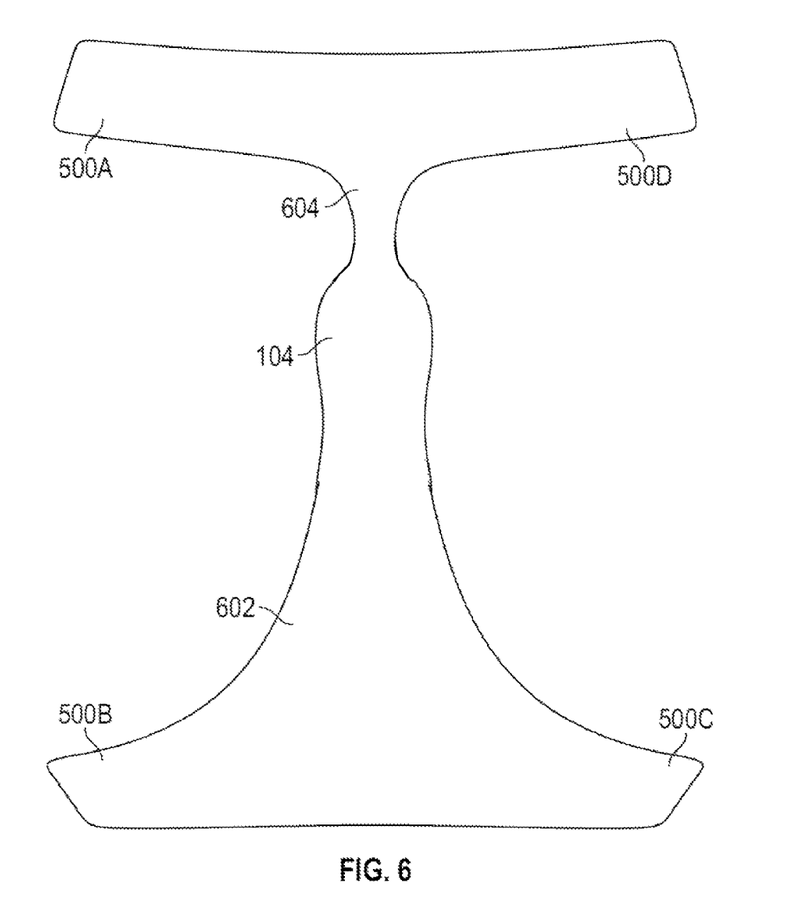
FIG. 6 representatively illustrates a top view of the convertible sanitary garment in an unfolded configuration in accordance with an exemplary embodiment of the present technology.
Figure 7:
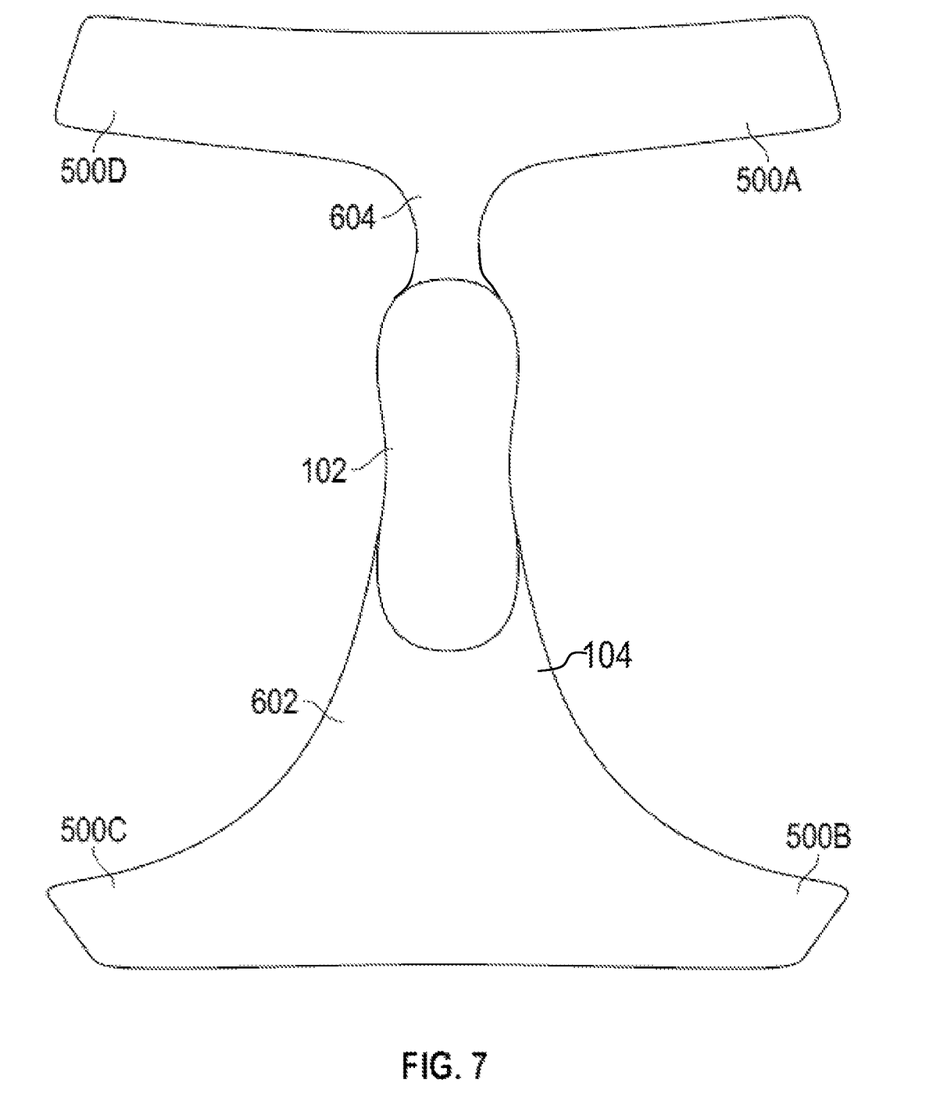
FIG. 7 representatively illustrates a bottom view of the convertible sanitary garment in an unfolded configuration in accordance with an exemplary embodiment of the present technology.

A second surface, opposite the first surface of the removable adhesive layer 108 and facing away from the garment portion 104, may comprise an adhesive material 304 configured to allow the convertible sanitary garment 100 to be attached to another garment such as a pair of underpants. A removable adhesive cover 106 may be used to protect the adhesive material 304 until the user chooses to use the convertible sanitary garment 100. This option of use allows the convertible sanitary garment 100 to be used in a manner consistent with prior art pads and napkins, or more specifically, once the adhesive cover 106 is removed the entire convertible sanitary garment 100 may be positioned against a pair of underpants like a traditional sanitary pad or napkin.

When used in this manner the garment portion 104 remains contained within the compartment area created by the removable adhesive layer 108. This is accomplished because the removable adhesive layer 108 remains connected to the liquid-impervious bottom sheet 1204 after the adhesive cover 106 is removed or otherwise separated from the removable adhesive layer 108 to uncover the adhesive material.

The adhesive cover 106 may comprise any suitable device or system for covering the adhesive material 304 such as a removable sheet, panel, or cover. The adhesive cover 106 may also comprise any suitable material that allows the convertible sanitary garment 100 to retain its flexibility during storage. For example, similar to the removable adhesive layer 108, the adhesive cover 106 may comprise a thin plastic sheet or fabric material that extends along at least a portion of the surface of the removable adhesive layer 108 covering the adhesive material 304.

When the removable adhesive layer 108 is detached from the liquid-impervious bottom sheet 1204 the garment portion 104 may be unfolded. For example, and referring now to FIGS. 5-8, in one embodiment, the garment portion 104 may comprise a front portion 602 and a back portion 604 that can be unfolded outwardly from the crotch section. The front and back portions 602, 604 may each comprise a pair of tabs 500 configured to be connected to form the wearable undergarment for use.

The front and back portions 602, 604 may comprise any suitable shape or size. For example, the front and back portions 602, 604 may comprise shapes that correspond to front and rear portions of a pair of panties. More specifically, the front portion 602 may comprise a substantially triangular shape having a first size determined according to desired amount of coverage for the front of a wearer's anatomy when the wearable garment is worn. The back portion 604 may also comprise a substantially triangular shape but have a larger overall size that is configured to cover the rear portion of the wearer's anatomy. The size and shape of the front and back portions 602, 604 may also be selected according to a desired style or cut of undergarment. For example, the front and back portions 602, 604 may comprise the corresponding front or rear portion of a pair of: briefs, bikini, French cut, boy short, or the like.

Figure 8:
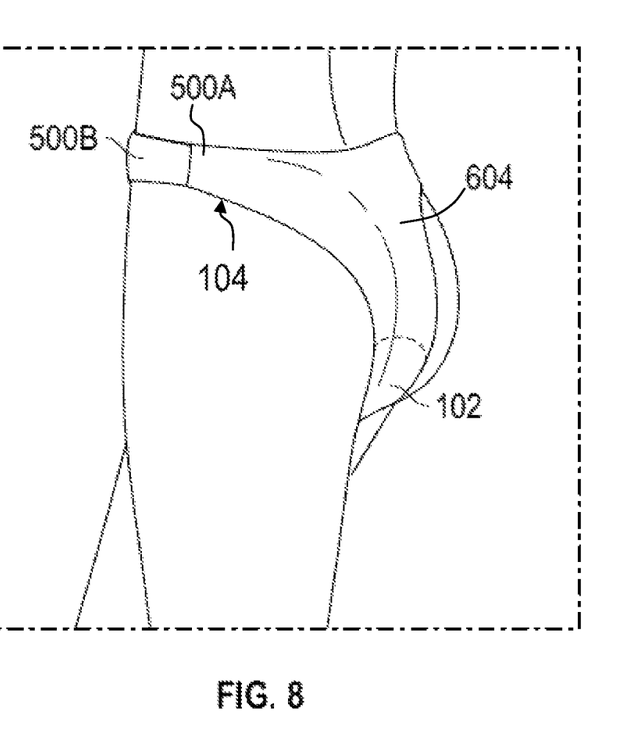
FIG. 8 representatively illustrates a side view of the convertible sanitary garment in accordance with an exemplary embodiment of the present technology.

The tabs 500 may be positioned to allow the wearer to selectively couple the tabs 500 together to form the wearable garment. For example, the front portion 602 may comprise a first tab 500B positioned at a first corner section and a second tab 500C positioned at a second corner location. The back portion 604 may comprise similarly located first and second tabs 500A, 500D at opposing first and second corner sections of the back portion 604. The first tab 500A of the back portion 604 may be connected to the first tab 500B of the front portion 602 to form a first side section of a waistband of the wearable garment. Similarly, the second tab 500D of the back portion 604 may be connected to the second tab 500C of the front portion 602 to form a second side section of the waistband to form a fully formed and wearable garment as shown in FIG. 8.

The tabs 500 may be configured in a way to allow the wearer to connect them together selectively adjust a waist size of the wearable garment providing for a more comfortable and customized fit. The tabs 500 may be connected together by any suitable method or device such as chemically or mechanically. For example, in one embodiment, the tabs 500 may comprise an adhesive disposed along a surface of the respective corner sections that bonds with the adhesive of a corresponding corner section to firmly fasten the tabs 500 together. The adhesive may be configured to allow the tabs 500 to be repeatedly attached and detached from each other or the adhesive may be selected to provide a single use bond. In an alternative embodiment, each tab 500 may comprise a mechanical fastening device such as a button, hook and loop fastener, or the like.

In an alternative embodiment, the garment portion 104 may comprise a fully formed wearable garment that does not require any assembly prior to use. For example, the garment portion 104 may comprise a fully assembled pair of undergarments that are folded inward towards the crotch section and secured in place by the removable adhesive layer 108 as detailed above. Once the removable adhesive layer 108 is detached from the liquid-impervious bottom sheet 1204, the garment portion 104 is immediately ready for use once unfolded. In this embodiment, the garment portion 104 may have to be turned "right side" out prior to use so that the absorbent layer 102 is positioned correctly while the wearable garment is being worn.

Figure 9:
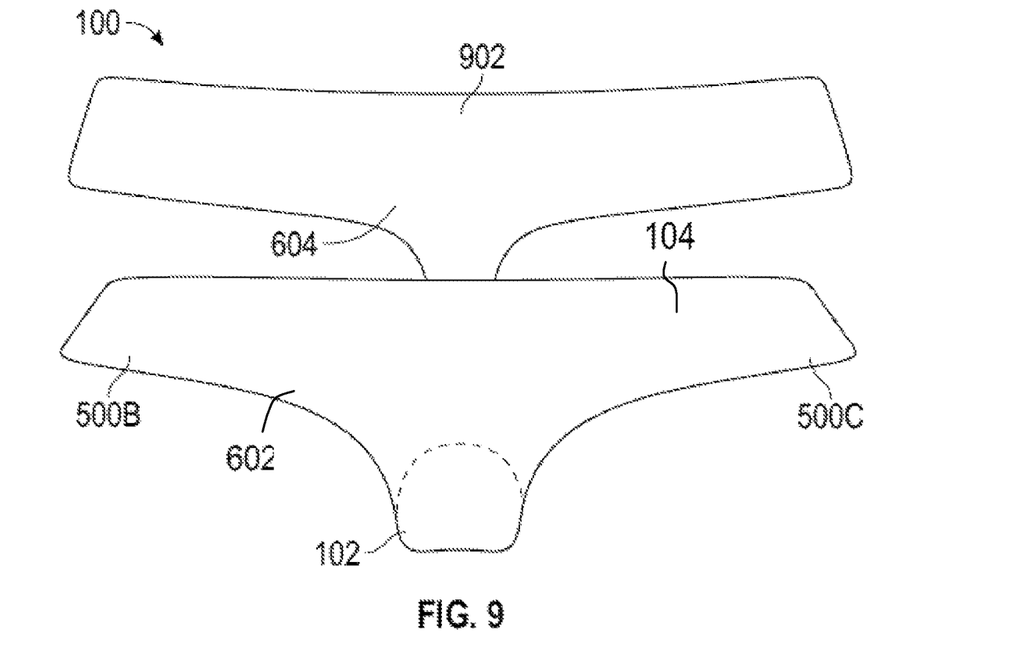
FIG. 9 representatively illustrates a front view of an alternative embodiment of the convertible sanitary garment in accordance with an exemplary embodiment of the present technology.
Figure 10:
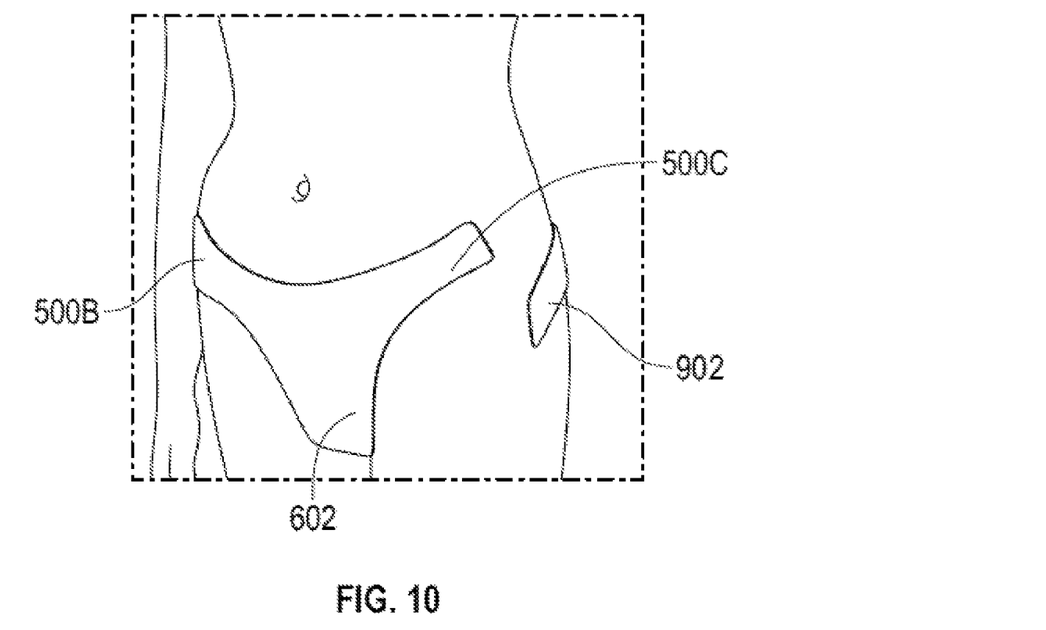
FIG. 10 representatively illustrates a front perspective view of the convertible sanitary garment of FIG. 9 in a worn position in accordance with an exemplary embodiment of the present technology.
Figure 11:
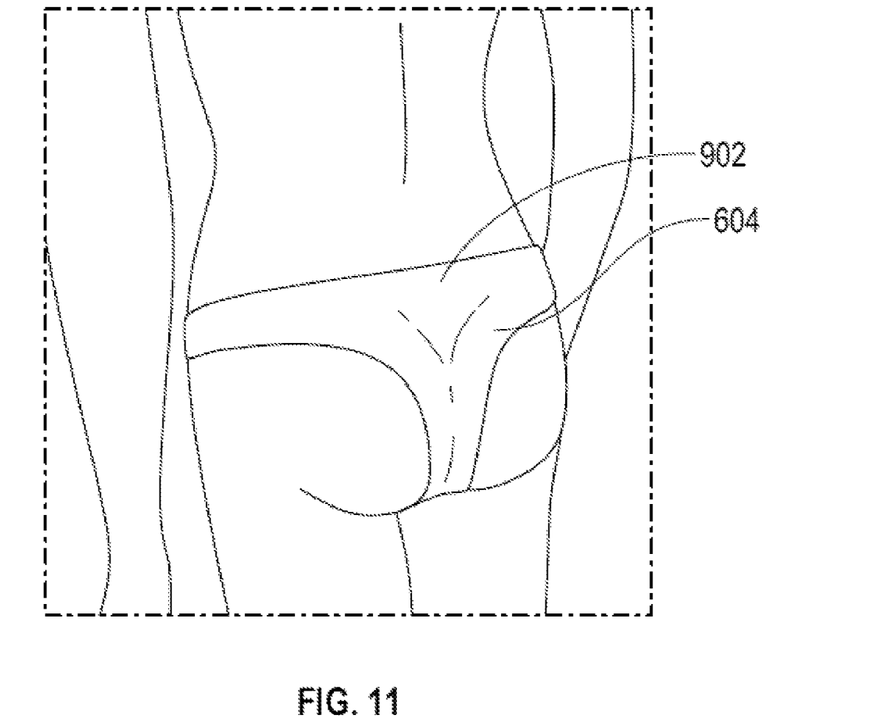
FIG. 11 representatively illustrates a rear perspective view of the convertible sanitary garment of FIGS. 9 and 10 in a worn position in accordance with an exemplary embodiment of the present technology.

Referring now to FIGS. 9-11, in yet another embodiment, the tabs 500 and/or a waist portion may be configured to be secured directly to the wearer's skin. For example, the forward facing tabs 500B, 500C extending from the front portion 602 may comprise an adhesive that is adapted to stick or adhere to the wearer's skin at or near a forward facing portion of the wearer's hip bone or waistline. A rear waistline portion 902 disposed along an upper edge of the back portion 604 may also comprise an adhesive that is configured to secure the back portion 604 to the wearer's skin at or near the wearer's rear waistline, tail bone, or any other suitable location. The rear waistline portion 902 may also extend at least part way towards the forward facing tabs 500B, 500C but not touch or otherwise be coupled to the forward facing tabs 500B, 500C. This configuration leaves a gap between the forward facing tabs 500B, 500C and the rear waistline portion 902 as shown in FIG. 10.

Figure 14:
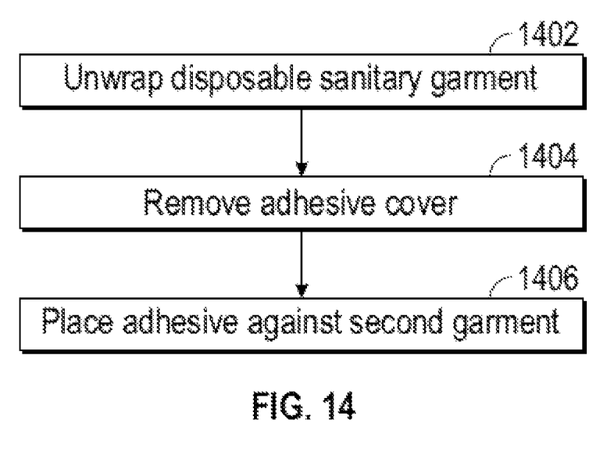
FIG. 14 representatively illustrates a flow chart for a first method of using the convertible sanitary garment in accordance with an exemplary embodiment of the present technology.

As described above, the manner in which the removable adhesive layer 108 and the adhesive cover 106 are arranged allow for the convertible sanitary garment 100 to be used in at least two ways. First, and referring now to FIG. 14, removal of only the adhesive cover 106 allows the convertible sanitary garment 100 to be used in the same manner as a traditional sanitary pad or napkin. For example, the convertible sanitary garment 100 may first be unwrapped from a sanitary package (1402). The adhesive cover 106 may then be removed from the removable adhesive layer 108 to expose the adhesive material (1404). The adhesive material may then be pressed against another garment such as a pair of underpants such that the liquid pervious top sheet 1202 of the absorbent layer 102 is positioned against the wearer's skin during use (1406).

Figure 15:
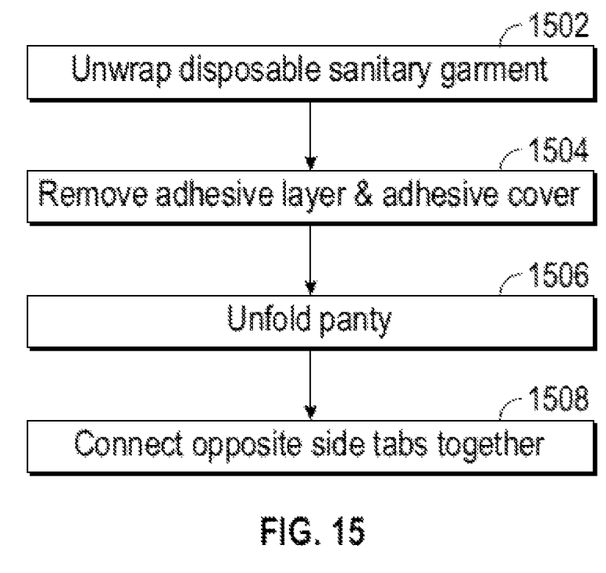
FIG. 15 representatively illustrates a flow chart for a second method of using the convertible sanitary garment in accordance with an exemplary embodiment of the present technology.

Alternatively, and referring now to FIG. 15, the convertible sanitary garment 100 may be worn in place of a pair of undergarments and disposed of after use. For example, as above, the convertible sanitary garment 100 may first be unwrapped from a sanitary package (1502). The removable adhesive layer 108 may then be removed from the liquid impervious bottom sheet 1204 of the absorbent layer 102 to expose the garment portion 104 (1504). The garment portion 104 may then be unfolded outwardly away from the absorbent layer 102 for use (1506). Mating tabs 500 on opposing front and rear portions 602, 604 of the garment portion 104 may be connected together to form the wearable garment (1508).

These and other embodiments for methods of creating a convertible sanitary garment may incorporate concepts, embodiments, and configurations as described above. The particular implementations shown and described are illustrative of the technology and its best mode and are not intended to otherwise limit the scope of the present technology in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

The description and figures are to be regarded in an illustrative manner, rather than a restrictive one and all such modifications are intended to be included within the scope of the present technology. Accordingly, the scope of the technology should be determined by the generic embodiments described and their legal equivalents rather than by merely the specific examples described above. For example, the components and/or elements recited in any apparatus embodiment may be assembled or otherwise operationally configured in a variety of permutations to produce substantially the same result as the present technology and are accordingly not limited to the specific configuration recited in the specific examples.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present technology, in addition to those not specifically recited, may be varied or otherwise particularly adapted to specific environments, manufacturing specifications, design parameters or other operating requirements without departing from the general principles of the same.

The present technology has been described above with reference to exemplary embodiments. However, changes and modifications may be made to the exemplary embodiments without departing from the scope of the present technology. These and other changes or modifications are intended to be included within the scope of the present technology, as expressed in the following claims.

The invention claimed is:

1. A convertible sanitary garment, comprising:
    an absorbent layer comprising:
        a liquid pervious top surface; and
        a liquid impervious bottom surface;
    a garment portion coupled to the liquid impervious bottom surface;
    a removable adhesive layer configured to enclose the garment portion within an area defined by the liquid impervious bottom surface, comprising:
        a first surface facing the garment portion, wherein a portion of the first surface is removably coupled to an outer periphery of the liquid impervious bottom surface; and
        an opposing second surface facing away from the garment portion, wherein at least a portion of the second surface comprises an adhesive,
        wherein the removable adhesive layer is configured to be disconnected from the liquid impervious bottom surface to allow the garment portion to be unfolded and worn; and
    a removable adhesive cover disposed along and covering the adhesive on the second surface of the removable adhesive layer.

2. A convertible sanitary garment according to claim 1, wherein the garment portion comprises:
    a crotch section coupled to and covering the liquid impervious bottom surface;
    a forward portion configured to be unfolded to extend away from the crotch section, wherein the forward portion comprises:
        a first tab on a first side; and
        a second tab on a second side; and
    a back portion configured to be unfolded to extend away from the crotch section opposite the forward portion, wherein the back portion comprises:
        a first tab on a first side; and
        a second tab on a second side, wherein:
            the first tab of the forward portion and the first tab of the back portion are configured to be coupled together to form a first side of the garment portion; and
            the second tab of the forward portion and the second tab of the back portion are configured to be coupled together to form a second side of the garment portion.

3. A convertible sanitary garment according to claim 2, wherein the first tab of the forward portion and the first tab of the back portion and the second tab of the forward portion and the second tab of the back portion are coupled together adhesively.

4. A convertible sanitary garment according to claim 2, wherein the first and second tabs of the forward and back portions are positioned along a waistline of the garment portion.

5. A convertible sanitary garment according to claim 2, wherein the crotch section comprises the same shape as the liquid impervious bottom surface.

6. A convertible sanitary garment according to claim 1, wherein the absorbent layer comprises an absorbent core material disposed between the liquid pervious top surface and the liquid impervious bottom surface.

7. A convertible sanitary garment according to claim 1, wherein the garment portion is adhered to the liquid impervious bottom surface.

8. A convertible sanitary garment according to claim 1, wherein the liquid impervious bottom surface is woven into the garment portion.

9. A convertible sanitary garment according to claim 1, wherein the garment portion comprises:
    a crotch section coupled to and covering the liquid impervious bottom surface;
    a forward portion configured to be unfolded to extend away from the crotch section, wherein the forward portion comprises:
        a first tab on a first side; and
        a second tab on a second side; and
    a back portion configured to be unfolded to extend away from the crotch section opposite the forward portion, wherein the back portion comprises a rear waistline portion, wherein:

the first and second tabs of the forward portion each comprise an adhesive surface arranged to be affixed proximate a forward portion of a user's hip bone; and the rear waistline portion comprises an adhesive surface that is arranged to be affixed on the user rearward of the first and second tabs.

10. A convertible sanitary garment according to claim 9, wherein the first and second tabs of the forward portion and the rear waistline portion are independently affixed to the user.

11. A convertible sanitary garment according to claim 9, wherein the crotch section is removably coupled to the liquid impervious bottom surface to allow for the selective decoupling of the garment portion from the absorbent layer.

12. A convertible sanitary garment, comprising:
   a liquid pervious top sheet;
   a liquid impervious back sheet;
   an absorbent core material disposed between the liquid pervious top sheet and a first surface of the liquid impervious back sheet;
   a garment portion coupled to a second surface of the liquid impervious back sheet;
   a removable adhesive layer coupled to an outer periphery of the liquid impervious back sheet to form a sealed pouch portion for enclosing the garment portion, wherein the removable adhesive layer is configured to be disconnected from the liquid impervious back sheet to allow the garment portion to be unfolded into a wearable form and comprises:
      a first surface facing the garment portion; and
      an opposing second surface facing away from the garment portion, wherein at least a portion of the second surface is covered with an adhesive; and
   a removable adhesive cover disposed along and covering the adhesive on the second surface of the removable adhesive layer, wherein the removable adhesive cover is configured to be removed to allow the adhesive on the second surface to be secured to another garment.

13. A convertible sanitary garment according to claim 12, wherein the garment portion comprises:
   a crotch section coupled to and covering the liquid impervious back sheet;
   a forward portion configured to be unfolded to extend away from the crotch section and comprising a first tab on a first side and a second tab on a second side; and
   a back portion configured to be unfolded to extend away from the crotch section opposite the forward portion and comprising a first tab on a first side and a second tab on a second side, wherein:
      the first tab of the forward portion and the first tab of the back portion are configured to be coupled together to form a first side of the panty; and
      the second tab of the forward portion and the second tab of the back portion are configured to be coupled together to form a second side of the panty.

14. A convertible sanitary garment according to claim 12, wherein the first tab of the forward portion and the first tab of the back portion and the second tab of the forward portion and the second tab of the back portion are coupled together adhesively.

15. A convertible sanitary garment according to claim 12, wherein the first and second tabs of the forward and back portions are positioned along a waistline of the garment portion.

16. A convertible sanitary garment according to claim 12, wherein the crotch section comprises the same shape as the liquid impervious bottom surface.

17. A convertible sanitary garment according to claim 12, wherein the garment portion is adhered to the second surface of the liquid impervious back sheet.

18. A convertible sanitary garment according to claim 12, wherein the liquid impervious back sheet is woven into the garment portion.

19. A convertible sanitary garment according to claim 12, wherein the garment portion comprises:
   a crotch section coupled to and covering the liquid impervious back sheet;
   a forward portion configured to be unfolded to extend away from the crotch section, wherein the forward portion comprises:
      a first tab on a first side; and
      a second tab on a second side; and
   a back portion configured to be unfolded to extend away from the crotch section opposite the forward portion, wherein the back portion comprises a rear waistline portion, wherein:
      the first and second tabs of the forward portion each comprise an adhesive surface arranged to be affixed proximate a forward portion of a user's hip bone; and
      the rear waistline portion comprises an adhesive surface that is arranged to be affixed on the user rearward of the first and second tabs.

20. A convertible sanitary garment according to claim 18, wherein the first and second tabs of the forward portion and the rear waistline portion are independently affixed to the user.

* * * * *